US008940524B2

(12) United States Patent
Cobb

(10) Patent No.: US 8,940,524 B2
(45) Date of Patent: Jan. 27, 2015

(54) EPISTEM GENEDRIVE

(75) Inventor: Ben Cobb, North Wraxal (GB)

(73) Assignee: Epistem Limited, Manchester (GB)

( * ) Notice: Subject to any disclaimer, the term of this patent is extended or adjusted under 35 U.S.C. 154(b) by 0 days.

(21) Appl. No.: 13/240,035

(22) Filed: Sep. 22, 2011

(65) Prior Publication Data

US 2012/0077259 A1 Mar. 29, 2012

(30) Foreign Application Priority Data

Sep. 24, 2010 (GB) .................................. 1016014.1

(51) Int. Cl.

| | |
|---|---|
| ***C12M 1/00*** | (2006.01) |
| ***C12M 3/00*** | (2006.01) |
| ***C12M 1/34*** | (2006.01) |
| ***B01L 7/00*** | (2006.01) |
| *B01L 9/00* | (2006.01) |

(52) U.S. Cl.

CPC .... *B01L 7/52* (2013.01); *B01L 9/54* (2013.01); *B01L 2200/14* (2013.01); *B01L 2300/1822* (2013.01); *B01L 2300/1827* (2013.01); *B01L 2300/1844* (2013.01); *B01L 2300/185* (2013.01)

USPC .................. 435/287.2; 435/283.1; 435/287.1; 435/288.1; 435/288.2

(58) Field of Classification Search

USPC ........................................... 435/283.1–309.4

See application file for complete search history.

(56) References Cited

U.S. PATENT DOCUMENTS

2007/0077648 A1 4/2007 Okamoto et al.
2008/0124722 A1* 5/2008 Dromaretsky et al. ........... 435/6
2008/0274511 A1* 11/2008 Tan et al. ..................... 435/91.2
2009/0130719 A1 5/2009 Handique et al.
2009/0203120 A1* 8/2009 Shin et al. .................. 435/303.1
2009/0275113 A1* 11/2009 Maltezos et al. ........... 435/286.1
2010/0203595 A1 8/2010 Ward et al.
2011/0005932 A1* 1/2011 Jovanovich et al. .......... 204/453

OTHER PUBLICATIONS

International Search Report for PCT/GB2011/051787 dated Dec. 15, 2011.
Written Opinion for PCT/GB2011/051787 dated Dec. 15, 2011.

* cited by examiner

*Primary Examiner* — Nathan Bowers
*Assistant Examiner* — Lydia Edwards
(74) *Attorney, Agent, or Firm* — Choate Hall & Stewart, LLP; Brenda Herschbach Jarrell

(57) ABSTRACT

We describe a thermal cycler comprising a Peltier-type thermoelectric element used for cooling a sample block, and a non-Peltier-type heating device for heating the sample block. The cycler also includes a heat sink connected to the Peltier-type element by a heat pipe, which permits thermal energy to transfer from the Peltier-type element to the heat sink. This configuration operates more efficiently than conventional thermal cyclers which use Peltier-type elements for heating and cooling, and allows a more rapid cycling time as well as operation in a wider range of ambient temperatures. Certain embodiments utilise the Peltier-type element as a thermal gate to reduce thermal loss during heating when the Peltier-type element is switched off.

24 Claims, 4 Drawing Sheets

EPISTEM GENEDRIVE

PRIORITY CLAIM

The present application claims the benefit of priority under 35 USC 119 of previously regularly filed foreign application UK 1016014.1, filed on Sep. 24, 2010. The present application, filed on Sep. 22, 2011, is filed within twelve months from the date on which this foreign application was filed.

FIELD OF THE INVENTION

The present invention relates to a thermal cycler apparatus, for use in thermal cycling reactions. Aspects of the invention relate to methods for performing thermal cycling reactions.

BACKGROUND TO THE INVENTION

Thermal cycling applications are an integral part of contemporary molecular biology. For example, the polymerase chain reaction (PCR), which is used to amplify nucleic acids, uses a series of DNA melting, annealing, and polymerisation steps at different temperatures to greatly 'amplify' the amount of DNA in a sample. Other thermal cycling applications are also known.

A typical thermal cycling apparatus consists of a metal sample block containing an appropriate number of recesses to receive one or more reaction vessels. The sample block may be shaped to conform to a 96-well plate format or individual reaction-tubes that are generally 0.5 μl or 0.20 micro-centrifuge (Eppendorf) tubes. The metal block acts as a thermal mass that transfers its thermal energy to and from the reaction samples. In general thermal cycling energy is provided using a Thermoelectric Cooling (TEC) device, also commonly known as a Peltier Effect element (PE). A thermal cycling apparatus will generally also use a heat sink to assist in heat transfer to and from the Peltier and a large fan or the like, to remove the excess heat generated by the Peltier and transferred to the heat sink during cooling.

Peltier elements are solid-state devices that convert an electric current into a temperature gradient. They consist of two sides—a hot side and a cold side. The module acts as a heat pump in that it moves heat from the cold side to the hot side. Switching the direction of current flow will swap the hot and cold side states and regulating this current flow is used to cycle temperature of the sample block in order to provide the heating and cooling required for PCR. The hot side of the Peltier requires a method of removing that heat for the unit to function properly and to cool effectively. The more efficient the means of removing this heat from the hot side, the colder the cold side will operate and the more quickly the cold side will reach its optimum temperature for thermal transfer. This is limited by the mass of the heat sink used and the airflow of the fan used to remove the excess heat from the heat sink. In general a thermal cycler design becomes a compromise between the power rating for a specific heat sink, and the size of the heat sink and fans that can be accommodated in the design. In standard Peltier block thermal cyclers, the heat sink and fan units represent the majority of the unit and mass of the device.

Although convenient, such thermal cyclers suffer from a number of disadvantages. Key among these is that a Peltier element suffers from reduced efficiency when being used for both heating and cooling—for example, the Peltier device has significant thermal mass in the form of a heat sink which must itself be heated or cooled to enable efficient thermal transfer to the sample block. Achieving a reasonable efficiency for both heating and cooling is complex, and most thermal cycler designs must find a compromise between the heating and cooling functions of the Peltier element and the desired rate of thermal transfer to the sample block. As a consequence of this compromise, conventional thermal cyclers typically achieve a maximum heating or cooling rate of no more than 3 degrees Celsius per second and have a high power overhead to achieve these modest rates of performance.

The present invention provides an alternative thermal cycler arrangement.

SUMMARY OF THE INVENTION

According to the present invention, there is provided a thermal cycler comprising:

- a sample block for receiving a sample;
- a Peltier-type thermoelectric element adjacent the sample block, configured for cooling the sample block;
- a non-Peltier-type heating device adjacent the sample block, configured for heating the sample block;
- a heat sink, separated from the sample block and Peltier-type element; and
- a heat pipe connecting the heat sink to the Peltier-type element, which permits thermal energy to transfer from the Peltier-type element to the heat sink.

A thermal cycler according to the present invention separates the heating and cooling functions, allowing each to be optimised for the desired function. Further, the use of separate heater and cooler elements means that the thermal mass of the heat sink need not influence the performance of the Peltier and the efficiency of heating and cooling the sample block. In addition, a conventional heating element, for example an electrical resistance heating element, is in general more efficient than a Peltier-type element used for both heating and cooling; the Peltier-type element is more efficient when used for cooling only or when heating only.

In the preferred arrangement, the sample block is sandwiched between the Peltier-type element and the non-Peltier-type heating device; for example, the element and the device are located on opposed faces of the sample block. Conventional thermal cycler devices use a stacked arrangement, in which the sample block is positioned above the Peltier element, which is positioned above the heat sink, which is positioned above the cooling fans. Sample tubes are loaded into the sample block from above. This conventional arrangement means that there is no position in which a non-Peltier-type heater may be conveniently located, other than between the sample block and the Peltier element, which would further reduce efficiency due to the need to cool through the heater.

The cycler may further comprise an optics assembly—for example, including a light source and light detector, optionally with one or more lenses. This allows the cycler to be used in detecting fluorescence or other signal from a reaction as the reaction proceeds in real time. The light source and light sensor may encompass any electromagnetic radiation, not merely visible light. The cycler may also comprise filters to restrict light of particular wavelengths. The cycler may further comprise a second light source; this allows for a relatively low-cost two-label detection system, where the two sources illuminate at different wavelengths. Where the cycler is intended to use a plurality of samples or reaction vessels in each cycling reaction, the cycler may conveniently comprise at least one light source/sensor combination for each sample.

In preferred embodiments of the invention, the light source is an LED or similar, while the light sensor is a photodiode or the like. The sensor is conveniently a log-response detector, which allows for a wider dynamic range, and a wider copy number of nucleic acids which can be detected. This arrangement allows for simple, robust components to be used without the requirement for lenses or complex optics arrangements. Such a source/sensor combination has been found to be sufficient to obtain qualitative information on the progress of a reaction (for example, that amplification is occurring). For many applications, such data is sufficient, and it is not necessary to quantitate the progress of the reaction.

The use of an LED/photodiode arrangement also reduces the need for critical positioning or distancing of the source and sensor with respect to the sample, again thereby making the cycler more robust. Conveniently the source and sensor operate at different wavelengths of light; for example, a preferred source is an LED emitting light at 490 nm, while a preferred sensor is most sensitive to light at 530 nm. This is consistent with typical fluorophores used in biochemical reactions. Modulated illumination of the LED or LEDs can be used, in order to help remove noise and background from the signal.

Where the sample block is sandwiched between the Peltier-type element and the heating device, the sample block will preferably be sized and shaped to receive multiple sample tubes arranged in a linear manner, or a strip of sample tubes. This ensures uniform heating and cooling. The Peltier and heating elements are preferably located above and below the sample block in normal use, and the sample block is orientated to receive the sample holder from the side (rather than from above as with conventional cyclers). This arrangement has an additional advantage over conventional arrangements, in that a side opening means that it is less likely that foreign objects will fall into the opening and either contaminate the sample, or obscure any optical assembly which may be present within the cycler.

The construction of the sample block sandwiched between heating element and Peltier allows optimum shape and size to receive a sample holder and to provide thermal transfer whilst enabling a design with minimal mass. In combination with high surface to area ratio tubes, thermal transfer rates to the reaction from the sample block is highly efficient.

The sample holder need not be received generally horizontally; an angle of less than 90 degrees may be sufficient, for example, less than 80, 70, 60, 50, 45, 40 degrees.

The sample block may be removable from the thermal cycler; this allows use of replaceable or interchangeable blocks, for example to accommodate different sizes or arrangements of sample tubes.

The non-Peltier-type heating device may be any suitable heater, and is preferably an electrical resistance heater. Other heating devices may be used. The heating device may include one or more openings to allow light to pass through the device; this allows a light source and detector combination to be used which is located outside the sample block/heater.

Preferably the Peltier-type element is configured so as to be deactivated when the heater is activated; and preferably also vice versa. When the heater is activated and the Peltier element deactivated, the element acts as a thermal insulator that restricts heat loss from the sample block to the heat pipe and heat sink assembly. This significantly reduces the time required to heat the sample block, and so improves utility. Uniquely, the arrangement of the Peltier in this configuration acts as a 'thermal gate', providing a block to thermal loss during heating when switched off, whilst also providing an efficient cooling pathway when it is switched on.

Heat is removed from the hot side of the Peltier during the cooling phase of the thermal cycle via a heat pipe. The heat pipe preferably has a generally flat cross section, and may include micro-channel pipes containing acetone, or other cooling fluid. For example, Flat Cool Pipes from Amec Thermasol are suitable. Conventional heat pipes are typically based on round section copper pipes filled with water as a cooling fluid; these conventional pipes are less efficient than the preferred pipes, which also provide a much more compact footprint. With conventional heat pipes, the fan and heat sink may need to be stacked above the block which leads to considerable height of the unit. Flat Cool Pipes or similar allow the lateral, sequential positioning of components where the conventional method is limited to vertical stacking of components. This provides a compact positioning of parts. Critically it allows the heat sink to be arranged below the heat pipe that provides a highly efficient space footprint compared to conventional assemblies.

The heat pipe is preferably generally S-shaped, with the upper section contacting the heat sink, and the lower section contacting the Peltier element. The upper section is inclined (preferably around 20°, but in certain embodiments up to 90°) and the lower section is generally horizontal (preferably around 0°), but in certain embodiments up to 90°. The lower section is preferably smaller in area (for example, less than 10%, 20%, 30%, 40, 50% in area) of the upper section. For maximum efficiency at least the last 20% of the heat pipe is preferably inclined to be higher than the lower part where the heat is being generated, though in general greater than 50% of the heat pipe is inclined to provide the upper section. This allows efficient thermal transfer from the heat source, and also allows re-circulation of the cooling fluid within the pipe. Of course, it will be appreciated that the use of an S-shaped heat pipe is not essential to the invention, and that other shapes, including generally horizontal pipes, may be used.

The upper section of the heat pipe is connected to a heat sink, which may optionally also comprise an axial fan. This is used to remove excessive heat generated and transferred to the upper section of the heat pipe. The heat sink may be of any convenient form or material, but optionally it will be a forged aluminium pad with pin fins. Pins are preferably arranged in a 'dense' format of greater than 16 pins per $cm^2$.

Heat is removed from the heat sink using a high airflow fan, typically with airflow greater than 10, 20, 30 or 40 CFM (cubic feet per minute). Airflow via direct impingement is used to remove excess heat from the heat sink and is directed out of the device. Where alternative 'fin' heat sinks are used, axial, blower, tangential, or any convenient fan may provide the required airflow.

The cycler may further comprise a computer processor, which may be used for any or all of monitoring and controlling the light source and detector, temperature regulation, the cycling program, and the like. The processor is conveniently user-programmable, to allow selection of appropriate cycling programs for particular reactions. For example, the cycler may comprise a user interface, such as a keypad or touchscreen, allowing a desired cycling program to be selected, input or edited.

The computer processor may be mounted on a substrate, such as a circuit board or a PCB. In preferred embodiments of the invention, the remaining components of the cycler—for example, the Peltier-type element, the heater, the sample block, and the heat sink and pipe—are secured to the substrate. For example, the components may be bolted to the substrate. This allows for ease of construction and assembly, and permits a smaller footprint for the cycler. Of course, not all of the components need be secured directly to the substrate; some of the components may be secured to others (for example, the heater may be secured to the substrate, with the sample block secured to the heater and the Peltier element secured to the sample block). A casing may enclose the substrate and the remaining components.

DETAILED DESCRIPTION OF THE INVENTION

Figure 1:
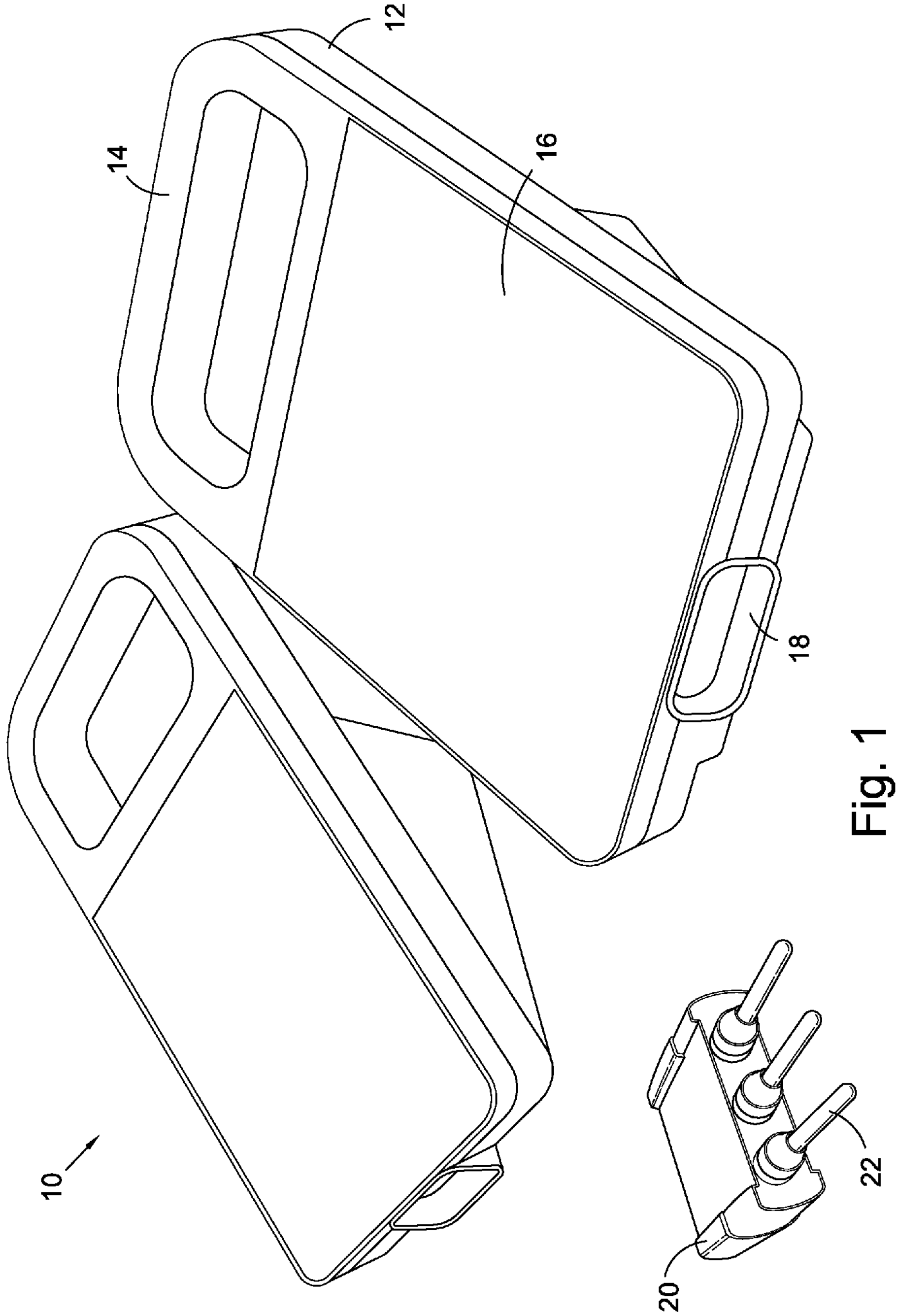
FIG. 1 shows an external view of a thermal cycler in accordance with an embodiment of the invention.

Referring first of all to FIG. 1, this shows an exterior view of a thermal cycler in accordance with the present invention. The cycler 10 includes an outer casing 12 formed with a carrying handle 14. The upper surface of the casing 12 is provided with a touchscreen interface 16 allowing the user to operate the cycler. The front of the casing provides an opening 18 into which can be inserted a sample holder 20, which includes (in this embodiment) three sample tubes 22 of thin-walled plastic.

Figure 2:
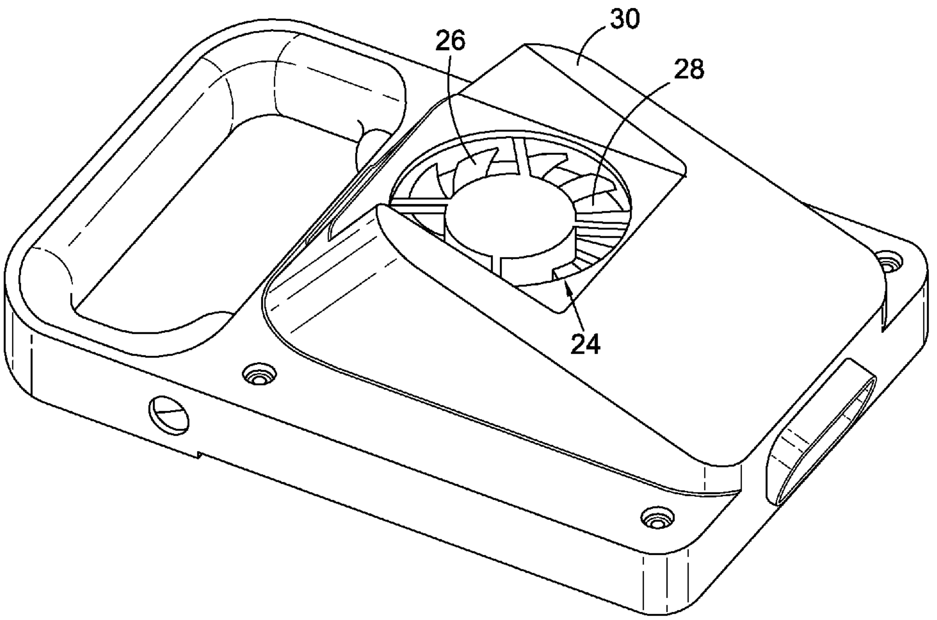
FIG. 2 shows an external view of the underside of the thermal cycler of FIG. 1.

The underside of the cycler 10 is shown in FIG. 2. The outer casing includes an opening 24 within which is mounted a cooling fan 26 which is adjacent a heat sink 28. The casing is formed with supports 30 which raise the fan 26 off the bench-top, allowing air to circulate.

Figure 3:
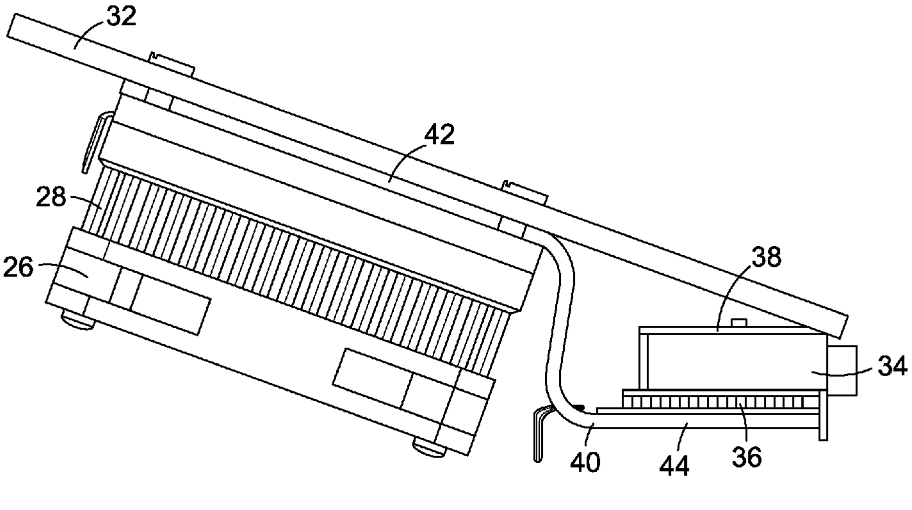
FIG. 3 shows a side view of the internal chassis components of the thermal cycler of FIG. 1.

The internal architecture of the cycler 10 is shown in FIG. 3. The outer casing 12 is not shown in this figure. A PCB substrate 32 is provided, on which are mounted the various electronic components needed to control and operate the cycler (for example, operating the user interface via the touchscreen; activating the heating and cooling elements; and operating the optical assembly). Secured to the substrate 32 via bolts 46 are the heat sink 28 and fan 26 assembly. Also secured to the substrate 32, but separated from the heat sink 28, is the sample block 34.

A Peltier element 36 is mounted beneath the sample block 34, in thermal contact therewith. Above the sample block 34 is an electrical resistance heater 38.

The Peltier element 36 is secured to a heat pipe 40, of the flat-section type formed with micro channels, using acetone as a coolant. The heat pipe 40 is generally S-shaped, and includes an upper section 42 in contact with the heat sink 28 and fan 26, and a lower section 44 in contact with the Peltier element 36. The upper section 42 is inclined at around 20°, while the lower section 44 is generally horizontal (at around 0°). The lower section 44 is around half the area of the upper section 42.

Figure 4:
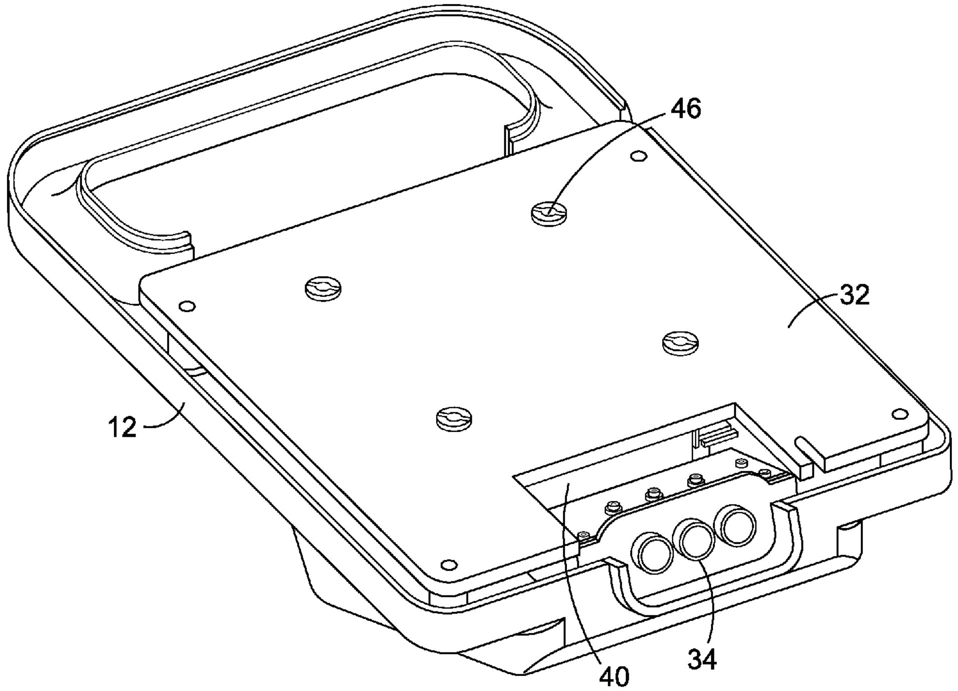
FIG. 4 shows an internal view of the thermal cycler of FIG. 1.
Figure 5A:
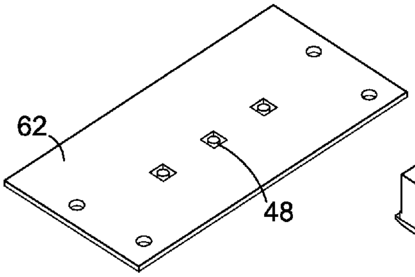
FIG. 5 shows the construction of the optical assembly and sample block of the thermal cycler of FIG. 1.
Figure 5B:
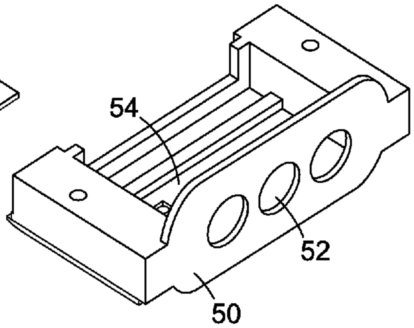
Figure 5C:
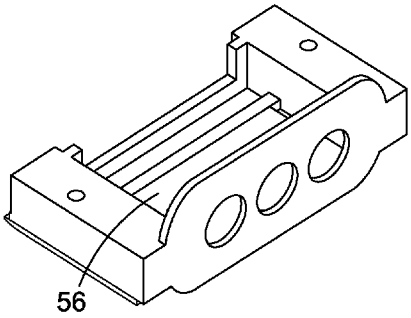
Figure 5D:
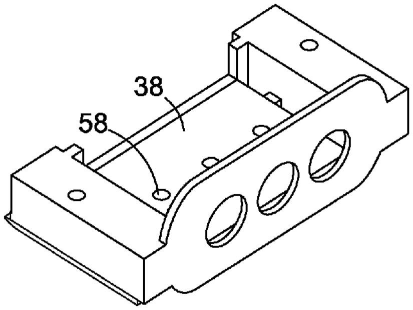
Figure 5E:
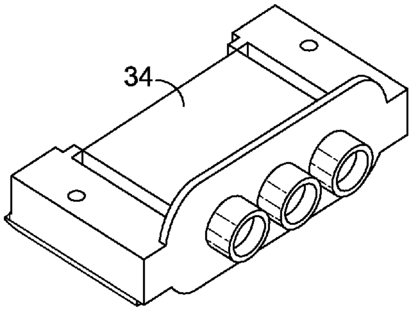
Figure 5F:
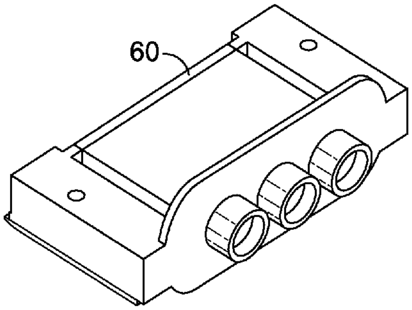

A view of the internal chassis is shown in FIG. 4. The substrate 32 carries the electronic components and processor needed to operate the cycler, while the remaining components are secured to the substrate 32 with bolts 46 or other fasteners. In this figure, a portion of the heat pipe 40 and the sample block 34 can be seen. The whole assembly can be simply mounted within the casing 12 for ease of manufacture.

The sample block assembly 34 is shown in more detail in FIG. 5. The block includes various components of the optical assembly (not shown in the other figures). A PCB 62 including three LEDs 48 is located within an optics assembly former 50, which includes three apertures 52 for receiving sample tubes, and an opening 54 for allowing light from the LEDs to pass. A 490 nm glass excitation filter 56 is placed in the opening above the LEDs 48, and the electrical heater 38 above the filter. The heater 38 includes three apertures 58 aligning with the LEDs. The sample block 34 is then placed in the former 50, and a 535 nm glass emission filter 60 placed at the rear of the sample block 34. The sample block may include apertures aligning with the LEDs and the emission filter, or may be transparent to light of the appropriate wavelength, or may include waveguides in suitable locations. The whole assembly may then be put together with the other components of the cycler.

In use, the cycler operates as follows. A user may program a desired cycling program using the touchscreen interface 16. This causes the control electronics to operate the components in the appropriate manner. A sample may then be loaded into the sample tubes 22 of the sample holder 20, and the holder then inserted into the sample block 34 via opening 18.

When the user presses a "START" icon (or similar) on the touchscreen, the heater 38 and Peltier element 36 are operated in an appropriate manner. The heater 38 is first activated to raise the temperature of the sample to a desired first temperature. Simultaneously the Peltier element 36 is deactivated, such that it acts as a thermal insulator between the sample block and the heat pipe 40, retaining heat within the sample block. When the sample block has reached the desired temperature for the desired time, the heater 38 may be deactivated, and the Peltier element 36 activated. The Peltier element 36 is operated so as to cool the sample block 34; heat is transferred from the sample block to the heat pipe 40. The heat pipe 40 then transfers heat from the lower section 44 to the upper section 42; heat is then dissipated via the heat sink 28 and fan 26. The cycle then repeats as desired.

In addition to this, the optics assembly may also be used to monitor the progress of the cycling reaction, either while cycling, or afterwards. The LEDs are actuated to illuminate the sample; emitted light is then detected by a light sensor. The intensity or simply the presence or absence of emitted light may be monitored either over time or at a particular time point. This allows for real time PCR to be carried out.

The cycler as described herein has several advantages over conventional prior art cyclers. Firstly, overall efficiency is improved by separating the heating and cooling functions, and using a non-Peltier heater. The use of a heat pipe to remove waste heat from the Peltier element, in combination with the separation of heating and cooling functions and the use of the Peltier element as a "gate" when the heater is activated, permits physical separation of the sample block/heater/cooler assembly and the heat sink/fan assembly, giving the cycler an improved physical footprint.

Further, the overall thermal profile of the 'thermal waste heat' is low. In a standard thermal cycler which uses a single Peltier element to both heat and cool, the heat sink can rise to in excess of 65 C to 85 C. With the present system the heat sink may only rise to 40 C-45 C, significantly lower. This in part is due to the recycling of energy within the linear flat heat pipe which has not been used in PCR instruments previously. The heat pipe ensures an efficient removal of heat from the hot side of the Peltier during cooling, which re-cycles the thermal energy and rapidly cools the hot side of the Peltier. The heat energy released by the heat sink is much lower, and therefore the power requirement of the Peltier much less.

The whole assembly can then operate at multiple power inputs which is significant. For example, a portable, field based unit requires a very low power profile such that it may be powered by batteries. Cyclers in accordance with the present invention can run off less than 50 W total power and still provide cycle times for 30× cycles of under 30 minutes.

Increasing the power decreases the cycle times and does not over burden the heat exchange mechanism. The present design enables this 'multi-power' ability. 100 W input reduces the cycle times down to 20 minutes and 150 W reduces the times down to 15 minutes. In particular, in preferred embodiments of the invention in use, the cycler undergoes 30 or more standard cycles of 5 seconds each at 50°, 72° and 95° C. in under 30 minutes, when operated at a power of 50 W or less; 30 or more standard cycles of 5 seconds each at 50°, 72° and 95° C. cycles in under 20 minutes, when operated at a power of 100 W or less; or 30 or more standard cycles of 5 seconds each at 50°, 72° and 95° C. cycles in under 20 minutes, when operated at a power of 150 W or less.

By comparison, standard block thermal cyclers require >500 W, rapid block cyclers such as Finnzymes Piko thermal cycler require 180 W, and air cyclers such as the lightCycler 2.0 from Roche require 800 W.

In fact, in tests when operating a cycler of the invention at 50 W; the heat pipe varied between 47° C. to 57° C., with the heat sink at 40° C. constant. At 100 W; the heat pipe was at 50° C. to 60° C., and the heat sink at 48° C. constant. At 150 W; the heat pipe was at 53° C. to 63° C., and the heat sink 49° C. constant.

So with variable power delivery the cooling efficiency remains high and in all circumstances the heat sink does not exceed 50° C. meaning that vented air will sit significantly below 40° C. The benefit of this is that as the ambient temperature increases, the performance of the unit will remain unperturbed.

Another benefit of the system is that it is less sensitive to changing outside ambient temperatures, again because of the efficiency of the arrangement and because there are multiple routes to remove heat from the system. This is again important for portable units. So even in ambient temperatures in excess of 50 C the unit still returns similar thermal cycling times as conventional units. This is because the fan and heat sink have significant overhead so that if the ambient temperature goes up, more of the heat is removed from the system by the fan and heat sink, rather than the evaporative properties of the heat sink. In fact, we believe that certain embodiments of the invention may operate in ambient temperatures of up to 55 C or more, whereas standard Peltier cyclers can only operate to 30-40 C.

The configuration allows use of a low mass sample block made from aluminium or thermoelastomer polymers that have high thermal transfer properties; these allow flexibility in the block which means consumables do not get stuck and allows a good resistance fit which is not generally possible with solid blocks and long, thin walled tubes.

Other advantages of the present invention will be apparent.

The invention claimed is:

1. A thermal cycler comprising:

a) a sample block comprising:

(1) a first opposing side with a first external surface and a first internal surface; and (2) a second opposing side with a second external surface and a second internal surface;

the first and second opposing sides being connected to one another by a sample receiving side that includes one or more sample receiving ports arranged and constructed to receive a sample so that the sample extends longitudinally between the first and second internal surfaces;

b) a Peltier-type thermoelectric element in thermal contact with the first external surface of the first opposing side and configured for cooling the sample block;

c) a non-Peltier-type heating device in thermal contact with the second external surface of the second opposing side and configured for heating the sample block;

d) a heat sink, separated from the sample block and Peltier-type element; and e) a heat pipe connecting the heat sink to the Peltier-type element and permitting thermal energy to transfer from the Peltier-type element to the heat sink.

2. The cycler of claim 1 further comprising an optics assembly located adjacent to the sample so that a signal generated within the sample can be detected.

3. The cycler of claim 2 wherein the optics assembly comprises a light source and light detector, optionally with one or more lenses.

4. The cycler of claim 1 wherein the sample block is sized and shaped to receive multiple sample tubes arranged in a linear manner, or a strip of sample tubes.

5. The cycler of claim 1 wherein the sample block is sized and shaped to receive a sample holder from the receiving side when in use.

6. The cycler of claim 1 wherein the sample block is removably associated with the thermal cycler.

7. The cycler of claim 1 wherein the non-Peltier-type heating device is an electrical resistance heater.

8. The cycler of claim 1 wherein the non-Peltier-type heating device includes one or more openings to allow light to pass through the device.

9. The cycler of claim 1 wherein the Peltier-type element is configured so as to be deactivated when the non-Peltier-type heating device is activated.

10. The cycler of claim 1 further comprising a computer processor operationally associated with at least one of the Peltier-type element and the non-Peltier-type heating device so as to regulate activity of the Peltier-type element and/or the non-Peltier-type heating device through a desired time-temperature profile.

11. The cycler of claim 10 wherein the cycler comprises a user interface allowing user interaction with the computer processor.

12. The cycler of claim 10 wherein the computer processor is mounted on a substrate.

13. The cycler of claim 12 wherein the Peltier-type element, the heater, the sample block, and the heat sink and pipe are also secured to the substrate.

14. The cycler of claim 1 wherein the heat pipe has a flat cross section, and includes micro-channel pipes containing a cooling fluid.

15. The cycler of claim 1 wherein the heat pipe is generally S-shaped, with the upper section contacting the heat sink, and the lower section contacting the Peltier element.

16. The cycler of claim 15 wherein the upper section is inclined and the lower section is generally flat.

17. The cycler of claim 15 wherein the lower section is smaller in area than the upper section.

18. The cycler of claim 1 wherein, in use, the cycler undergoes 30 or more standard cycles of 5 seconds each at 50°, 72° and 95° C. in under 30 minutes, when operated at a power of 50 W or less.

19. The cycler of claim 1 wherein, in use, the cycler undergoes 30 or more standard cycles of 5 seconds each at 50°, 72° and 95° C. cycles in under 20 minutes, when operated at a power of 100 W or less.

20. The cycler of claim 1 wherein, in use, the cycler undergoes 30 or more standard cycles of 5 seconds each at 50°, 72° and 95° C. cycles in under 20 minutes, when operated at a power of 150 W or less.

21. The cycler of claim 1 further comprising one or more batteries to provide electrical power.

22. The cycler of claim 1 configured to operate at a selectable power input.

23. The cycler of claim 1 wherein, when the cycler undergoes 30 or more standard cycles of 5 seconds each at 50°, 72° and 95° C. in use at room temperature, the heat sink does not rise above 50° C.

24. The cycler of claim 1 wherein, when the cycler undergoes 30 or more standard cycles of 5 seconds each at 50°, 72° and 95° C. in use at room temperature, the heat pipe does not rise above 63° C.

* * * * *